United States Patent [19]

Livingston

[11] Patent Number: 5,302,750
[45] Date of Patent: Apr. 12, 1994

[54] METHOD FOR PRODUCING N-OCTADIENOL FROM BUTADIENE

[75] Inventor: Joel R. Livingston, Basking Ridge, N.J.

[73] Assignee: Exxon Chemical Patents Inc., Linden, N.J.

[21] Appl. No.: 67,196

[22] Filed: May 25, 1993

[51] Int. Cl.$^5$ .................... C07C 29/36; C07C 29/44; C07C 33/02
[52] U.S. Cl. ................ 568/909.5; 568/913; 568/922
[58] Field of Search ................ 568/909.5, 913

[56] References Cited

U.S. PATENT DOCUMENTS

| | | | |
|---|---|---|---|
| 4,356,333 | 10/1982 | Yoshimura et al. | 568/840 |
| 4,876,403 | 10/1989 | Cohen et al. | 568/913 M |
| 4,910,344 | 3/1990 | Pasternak et al. | 568/913 M |
| 4,962,243 | 10/1990 | Roeper et al. | 568/909.5 |
| 4,990,698 | 2/1991 | Wada et al. | 568/909.5 |
| 5,043,487 | 8/1991 | Thome et al. | 568/909.5 |
| 5,057,631 | 10/1991 | Tokitoh et al. | 568/909.5 |
| 5,118,885 | 6/1992 | Tokitoh et al. | 568/909.5 |
| 5,169,981 | 12/1992 | Packett | 568/909.5 |
| 5,230,801 | 7/1993 | Darnell et al. | 568/913 M |

FOREIGN PATENT DOCUMENTS

| | | | |
|---|---|---|---|
| 48427 | 3/1984 | Japan | 568/913 M |
| 1-268654 | 10/1989 | Japan | 568/913 M |
| 2201413 | 9/1988 | United Kingdom | 568/913 M |
| 9304029 | 3/1993 | World Int. Prop. O. | |

*Primary Examiner*—Joseph E. Evans
*Attorney, Agent, or Firm*—John J. Mahon

[57] ABSTRACT

A method for separating a water soluble noble metal catalyst from a crude reaction product of a noble metal-catalyzed process for preparing octadienol from butadiene in aqueous solution, in an aqueous emulsion or as an aqueous suspension, the crude reaction product including an aqueous phase containing a water soluble Group VIII noble metal-ligand complex catalyst, and an organic phase containing unreacted butadiene feed and an organic octadienol reaction product, which comprises: (a) contacting the crude reaction product with a hydrophobic membrane capable of allowing a substantial portion of the unreacted butadiene feed and organic octadienol reaction product to pass therethrough while retaining a substantial portion of the water soluble Group VIII noble metal-ligand complex catalyst; (b) removing unreacted butadiene feed and the organic octadienol reaction product which passes through the hydrophobic membrane as permeate; and (c) retaining the water soluble Group VIII noble metal-ligand complex catalyst as retentate.

27 Claims, No Drawings

METHOD FOR PRODUCING N-OCTADIENOL FROM BUTADIENE

This invention relates to a method for producing n-octadienol from butadiene and water in an aqueous solution in the presence of a water soluble Group VIII noble metal-ligand complex catalyst, wherein a hydrophobic membrane in a perstraction mode is used to separate the reaction product and feed from the metal-ligand complex catalyst.

BACKGROUND OF THE INVENTION

N-octadienol is useful as an intermediate for synthetic resin modifiers, agricultural chemicals, medicines, perfumes, and the like. Particularly, n-octanol which is obtained by reduction of n-octadienol is an important starting material for the preparation of di-n-octyl phthalate which is widely used as a plasticizer for polyvinyl chloride and similar polymers. Di-n-octyl phthalate is superior in use for various basic applications when compared to the conventional dioctyl phthalate derived from 2-ethylhexanol.

It has been proposed that n-octanol can be prepared by reacting butadiene with water in the presence of a palladium catalyst to synthesize n-octadienol followed by hydrogenation of n-octadienol (e.g., U.S. Pat. No. 3,670,032). However, according to the process disclosed in U.S. Pat. No. 3,670,032, both the rate of formation of n-octadienol and the selectivity toward it are extremely low so that the process is not suitable for the commercial production of n-octanol.

Since palladium is an extremely expensive metal, it is essential for the commercial production of n-octadienol by the reaction of butadiene with water to keep the activity of the catalyst stable for a prolonged period of time. In order to stabilize the activity of the catalyst, an addition of the phosphine in excess is necessary, but such excessive addition of the phosphine leads to unsatisfactory results in that, as mentioned above, both the rate of formation of and the selectivity toward n-octadienol are decreased.

Furthermore, in the synthesis of n-octadienol the product is generally isolated by direct distillation from the reaction mixture, and the distillation residue containing the catalyst components is recycled to the reaction system. However, the palladium catalyst has a tendency toward deterioration or metallization at distillation temperatures exceeding about 120° C. The deterioration and metallization of the palladium catalyst are serious problems from a commercial point of view, since these factors not only result in a decrease in the catalyst activity, but they make substantially impossible a continuous reuse of the catalyst. In order to suppress the deterioration and metallization of the palladium catalyst, it is necessary to conduct the distillation of products from the reaction mixture at a temperature of 120° C. or below, but in such cases other problems such as a build-up of high boiling by-products including octadienyl ether in the reaction system and a decrease in the distillation yield of n-octadienol may arise.

Thus, in order to achieve a truly industrial valuable method of n-octadienol synthesis by the reaction of butadiene and water in the presence of a palladium catalyst, it is essential to solve several problems which include the following: (1) the rate and the selectivity of the reaction must be improved to commercially acceptable levels, (2) catalyst life must be maintained over a prolonged period of time, and (3) the product must be isolated from the reaction mixture and the catalyst must be recycled without loss of catalyst activity.

U.S. Pat. No. 4,356,333 (Yoshimura et al.), which issued on Oct. 26, 1982, and which is incorporated herein by reference, attempts to overcome the problems set forth above by a process which comprises: (1) conducting the reaction of butadiene and water in an aqueous sulfolane solution having a water to sulfolane weight ratio of 20:80 to 70:30 and containing carbonate and/or bicarbonate ions in the presence of a palladium or a palladium compound catalyst, a monodentate phosphine ligand, and a monodentate tertiary amine; (2) subjecting the reaction mixture to solvent extraction; and (3) recycling the extraction residue containing the catalyst components to the first step, i.e., the reaction of butadiene and water.

The aqueous sulfolane solution permits easy separation of the product from the reaction mixture by means of extraction. That is, sulfolane is chosen as a co-solvent with water to avoid a reaction mixture that would be homogeneous, thus making catalyst recovery either very difficult or impossible. By the combined use of an aqueous sulfolane solution and a monodentate phosphine the palladium catalyst and sulfolane become substantially insoluble in the extractant and losses of the palladium catalyst, phosphine, tertiary amine and sulfolane because of their dissolution into the extractant layer become negligibly small. The desired product, i.e., n-octadienol, is subsequently separated from the reaction mixture by solvent extraction wherein the octadienol is extracted into the solvent and the catalyst and ligand are left in the aqueous layer. The extraction is generally carried out under an atmosphere of carbon dioxide or an inert gas in an extraction column. In order to remove trace amounts of catalyst and phosphine from the extract layer, the extract is washed with water or aqueous sulfolane. Thereafter, the catalyst is recycled to the synthesis step after being partially reactivated.

Moreover, since the problem of deterioration and metallization of the palladium catalyst due to heat and build-up of high boiling by-products can be overcome by the adoption of an extraction method, the catalyst activity can be kept more stable. Such advantages attributable to the extraction method can not be obtained in the absence of either the aqueous sulfolane solution or the monodentate phosphine. For example, when the ligand is triphenylphosphine substantial portions of the palladium and phosphine are extracted into the extractant layer even if the n-octadienol synthesis is carried out in an aqueous sulfolane solution, and hence the extraction procedure cannot be successfully applied.

The isolation of the octadienol from the extract layer is accomplished by distillation where it is separated from unreacted starting material, by-products and the extraction solvent.

The present inventor has discovered a novel means for simplifying the n-octadienol process of U.S. Pat. No. 4,356,333, and, in turn, substantially reducing the capital cost of the method in terms of system requirements and chemical additions. The present invention utilizes a hydrophobic membrane in a perstraction mode to separate as retentate the ligand and catalyst from a permeate of n-octadienol and unreacted butadiene feed. Thus, the need for extraction columns, distillation columns for extraction solvent separation and recovery from the reaction product, the extraction solvent itself and a catalyst re-activation section are avoided.

The use of a hydrophobic membrane and butadiene as the perstraction solvent allow more optimum synthesis conditions by eliminating the need for a reaction solvent that will separate easily in the extraction column; simplify the catalyst and ligand separation and recycle step; eliminate the extraction step thereby eliminating expensive extraction columns and the need for an extraction solvent and its subsequent wash step; reduce expensive distillation requirements to separate the extraction solvent from reaction products and to further purify it for recycle; and reduce losses of palladium and phosphine.

Although the reaction rate is satisfactory using the sulfolane, the rate would be faster if solvents or surfactants that promote phase transfer of the butadiene to the aqueous layer could be used. However, when phase transfer is promoted, emulsions of the mixture often result and solvent extraction becomes difficult. Membranes may be used to conveniently separate the organic-soluble constituents from the water soluble constituents from such mixtures. Thus, using the present invention, an optimum reaction system may be chosen without regard to the difficulties normally presented by emulsified reaction products.

The present invention also simplifies the catalyst and ligand separation and recycle step. In the conventional process, as discussed above, the catalyst and ligand may be recycled only after the reaction mixture is settled such that the aqueous layer contains the ligand and catalyst, and only after the catalyst has been re-activated. In the present invention, the ligand and catalyst may be recycled directly to the reactor along with any of the butadiene feed that may have permeated the membrane into the aqueous layer. No further treatment should be required.

Since the present invention eliminates the extraction step, expensive extraction columns, an extraction solvent and its subsequent wash step are no longer required. The effect of this is to reduce capital cost for the extraction column and wash column and reduce energy and solvent costs. Other costs eliminated are the capital cost for constructing and operating the distillation towers needed to separate the extraction solvent from the reaction products and to further purify it for recycle.

Finally, it is well known that reduction of process steps reduces the loss of feed, product and other components of the mixture such as, in the present case, expensive palladium and phosphine. This invention substantially reduces the number of steps required to isolate the product and recover and recycle the catalyst thus a reduction of losses is anticipated.

The present invention also provides many additional advantages which shall become apparent as described below.

SUMMARY OF THE INVENTION

A method for separating a water soluble noble metal catalyst from a crude reaction product of a noble metal-catalyzed process for preparing octadienol from butadiene in an aqueous solution, in an aqueous emulsion or as an aqueous suspension, the crude reaction product including an aqueous phase containing a water soluble Group VIII noble metal-ligand complex catalyst, and an organic phase containing unreacted butadiene feed and an organic octadienol reaction product, which comprises: (a) contacting the crude reaction product with a hydrophobic membrane capable of allowing a substantial portion of the unreacted butadiene feed and organic octadienol reaction product to pass therethrough while retaining a substantial portion of the water soluble Group VIII noble metal-ligand complex catalyst; (b) removing unreacted butadiene feed and the organic octadienol reaction product which passes through the hydrophobic membrane as permeate; and (c) retaining the water soluble Group VIII noble metal-ligand complex catalyst as retentate.

It is a further object according to the present invention to provide a method for producing n-octadienol which comprises:

(i) reacting butadiene with an aqueous solution in the presence of a water soluble Group VIII noble metal-ligand complex catalyst;

(ii) removing the water soluble Group VIII noble metal-ligand complex catalyst from the crude reaction product of step (i) by feeding the crude reaction product to a membrane separator which comprises a hydrophobic membrane capable of allowing a substantial portion of the octadienol reaction product and unreacted butadiene feed to pass therethrough while retaining a substantial portion of the water soluble Group VIII noble metal-ligand complex catalyst;

(iii) recovering the octadienol reaction product and unreacted butadiene feed as permeate;

(iv) retaining the water soluble Group VIII noble metal-ligand complex catalyst as retentate, wherein the hydrophobic membrane retains at least about 99% of the water soluble Group VIII noble metal-ligand complex catalyst; and (v) recycling the retained water soluble Group VIII noble metal-ligand complex catalyst to step (i).

An additional object according to the present invention which provides a method for producing n-octadienol wherein step (i) involves the reacting of butadiene with water in an aqueous sulfolane solution having a water to sulfolane weight ratio in the range of 20:80 to 70:30 and containing carbonate and/or bicarbonate ions in the presence of (A) palladium or a palladium compound, (B) a monodentate phosphine of the formula:

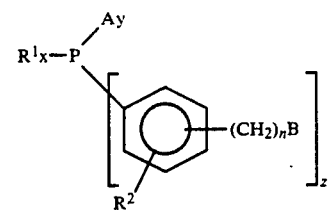

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$; wherein

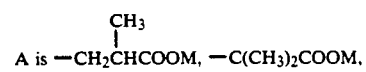

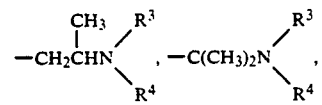

-continued a carbonate or bicarbonate of 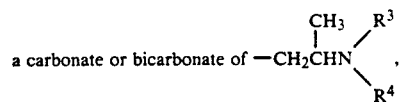 , or a carbonate or bicarbonate of 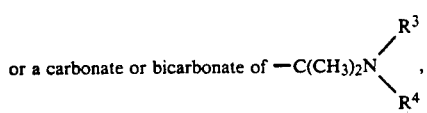 , and B is —SO$_3$M, —COOM, 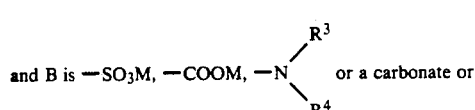 or a carbonate or bicarbonate of 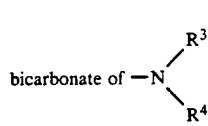

wherein R3 and R4 are each methyl, ethyl or n-propyl and M is an alkali metal in an amount of at least 6 moles per gram atom of palladium and (C) a monodentate tertiary amine having a basicity constant (pKa) of 7 or more in an amount of 1 to 50% by volume based on the sulfolane to form n-octadienol.

DESCRIPTION OF THE PREFERRED EMBODIMENTS

The process of the present invention comprises the steps of:

(i) reacting butadiene with water in an aqueous sulfolane solution having a water to sulfolane weight ratio in the range of 20:80 to 70:30 and containing carbonate and/or bicarbonate ions in the presence of (A) palladium or a palladium compound, (B) a monodentate phosphine of the formula:

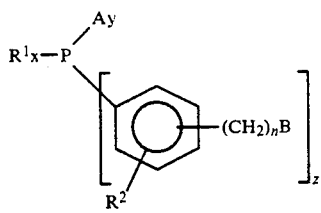

wherein R$^1$ is an aliphatic, alicyclic or substituted or unsubstituted aromatic hydrocarbon group having 1 to 8 carbon atoms; R$^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that x+y+z=3; wherein A is 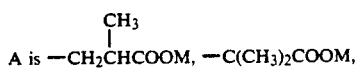

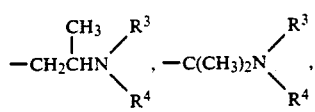

a carbonate or bicarbonate of 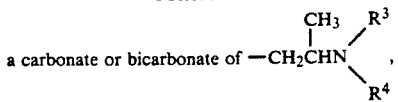 , or a carbonate or bicarbonate of 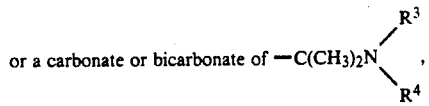 , and B is —SO$_3$M, —COOM, 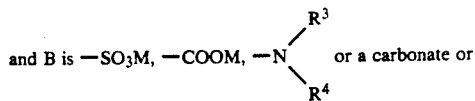 or a carbonate or bicarbonate of 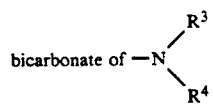

wherein R3 and R4 are each methyl, ethyl or n-propyl and M is an alkali metal in an amount of at least 6 moles per gram atom of palladium and (C) a monodentate tertiary amine having a basicity constant (pKa) of 7 or more in an amount of 1 to 50% by volume based on the sulfolane to form n-octadienol;

(ii) separating the water soluble Group VIII noble metal-ligand complex catalyst from the crude reaction product of step (i) by feeding the crude reaction product to a membrane separator which comprises a hydrophobic membrane capable of allowing a substantial portion of the octadienol reaction product and unreacted butadiene feed to pass therethrough while retaining a substantial portion of the water soluble Group VIII noble metal-ligand complex catalyst;

(iii) recovering the octadienol reaction product and unreacted butadiene feed as permeate;

(iv) retaining the water soluble Group VIII noble metal-ligand complex catalyst as retentate, wherein the hydrophobic membrane retains at least about 99% of the water soluble Group VIII noble metal-ligand complex catalyst; and (v) recycling the retained water soluble Group VIII noble metal-ligand complex catalyst to step (i).

Typically, the octadienol reaction product and unreacted butadiene which pass through the membrane are swept away by a sweep solvent of butadiene. Thereafter, the permeate may, optionally, be sent to a distillation section where the butadiene is recovered and recycled to step (i) and the octadienol is removed as product.

According to the process of the present invention, n-octadienol is produced at a high rate and at high selectivity even if the phosphine is added in large excess relative to the palladium. Moreover, the catalytic activity can be kept stable over a prolonged period of time, since the phosphine can be added in large excess relative to the palladium.

It has been found that in the reaction of step (i of the present process the use of an aqueous sulfolane solution having a water to sulfolane weight ratio of 20:80 to 70:30 as a reaction medium and of a monodentate phosphine having the particular structure shown as a ligand offers many advantages versus conventional reaction medium.

The noble metal catalyst is typically Pt, Rh, Ru or Pd. Preferably, any palladium or palladium compounds which have heretofore been proposed for use in the synthesis of n-octadienol can be used as the catalyst in the process of the present invention. Palladium in an active form may be supported on a carrier of low activity such as active charcoal. Examples of suitable palladium compounds include palladium acetylacetonate, π-allyl palladium acetate, π-allyl palladium chloride, palladium acetate, palladium propionate, palladium carbonate, palladium nitrate, palladium sulfate, palladium chloride, sodium chloropalladate, potassium chloropalladate, dichloroopalladate, potassium chloropalladate, dichlorobis(benzonitrile)palladium, bis(1,5-cyclooctadiene)palladium, bis-π-ally palladium, 1,5-cyclooctadiene)palladium chloride, and the like. The true catalytically active species are palladium complexes of low valency. Therefore, when a divalent palladium compound is used as the catalyst, it may be reduced with the phosphine or butadiene existing in the reaction system to form an active species, or alternatively the catalytically active species may be formed in the presence of a compound having a reducing ability either in the same reaction system or in another reaction vessel. The reducing agents useful for this purpose include alkali metal hydroxides, sodium borohydride, zinc powder, magnesium, hydrazine, alkali metal alkoxides, alkali metal carbonates, and the like. It is practical to use the reducing agents in an approximately stoichiometric amount required to change the valence of palladium. The amount of palladium or palladium compound used is not critical, but from the standpoint of commercial operation, palladium or a palladium compound is desirably used at a concentration of 0.1 to 50 milligram atom, preferably 0.5 to 20 milligram atom as palladium atom per liter of the aqueous sulfolane solution.

The aqueous phase preferably contains a water soluble phosphine in complex combination with a complex or catalytic precursor of the noble metal, e.g., sulfonated or carboxylated triaryl phosphines. The amphiphilic reagent is typically an anionic, nonionic or cationic surfactant or phase transfer agent such as a complex ammonium salt or a polyoxyethylene nonionic surfactant. The preferred ratio of aqueous phase to organic phase is 0.33:1 to 5:1, the ratio of $H_2$ to CO is 1:1 to 5:1, the content of precious metal in the aqueous phase is 100–500 ppm and the ratio of amphiphilic reagent to precious metal is up to 100:1 on a molar basis. It is preferable that the reaction be carried out at 300–10,000 kPa, especially 300–3,000 kPa and at a temperature in the range between about 40°–150° C.

In the monodenate phosphines of the formula set forth above, $R^1$ is a hydrocarbon group of 1 to 8 carbon atoms, more specifically an aliphatic hydrocarbon group such as methyl, ethyl, n-propyl, isopropyl, n-butyl, t-butyl, n-octyl or the like; an alicyclic hydrocarbon group such as cyclohexyl, methylcyclohexyl or the like or an aromatic hydrocarbon group such as phenyl, benzyl, tolyl or the like. The aromatic hydrocarbon group may be substituted by a methoxy, chloro, cyano or nitro group. The phosphine of the monodenate phosphine formula above in which B is —$SO_3M$ or —COOM is usually used as an alkali metal salt, which is preferably the sodium, potassium or lithium salt. Alternatively, the alkali metal salt may be replaced by the free sulfonic or carboxylic acid or its ester, which is reacted in the reaction system or another reaction vessel with an alkali metal hydroxide, bicarbonate, carbonate or the like to form the alkali metal salt.

Of the monodentate phosphine of the above formula, particularly preferred are di- or triaryl phosphine in which $R^1$ is an aromatic hydrocarbon group, n is 0 or 1, x is 0, 1 or 2, y is 0 or 1, z is 0, 1, 2 or 3 (with the proviso that y and z are not concurrently equal to 0 and that $x+y+z=3$).

An amino-containing phosphine is usually added to the reaction system as it is. Alternatively, since an amino phosphine is present in the form of its carbonate or bicarbonate salt in the reaction system, a carbonate or bicarbonate of an amino-containing phosphine may be previously prepared and added to the reaction system. The phosphines may be used either singly or in a combination of two or more thereof. The monodentate phosphine should be used in an amount of at least 6 moles, preferably at least 10 moles per gram atom of the palladium. There is no upper limit in a strict sense in the amount of the phosphine, but it is generally desirable that the phosphine is used in an amount of not more than 150 moles, preferably not more than 50 moles per gram atom of the palladium.

Alternatively, water soluble ligands from the following group of phosphine ligand may also be used: Na-p-(diphenylphosphino)benzoate, Na-m-(diphenylphosphino)benzenesulfonate, tri-(sodium m-sulfophenyl)-phosphine, and Na-p-(diphenylphosphino) benzenesulfonate.

The monodentate phosphines tend to oxidize into the corresponding phosphine oxides with oxygen existing in the reaction system in trace amounts and thereby lose their activities. It has been found that such oxidation of the monodentate phosphines can be inhibited by adding, in combination with such a phosphine, a bidentate phosphine in an amount of 0.3 to 3 moles per gram atom of the palladium. In addition, the use of such a bidentate phosphine permits the palladium catalyst to have an increased thermal stability, which results in stabilization of catalyst activity for a prolonged period. The bidentate phosphines may be used either singly or in a combination of two or more. Specific examples of bidentate are set forth in U.S. Pat. No. 4,356,333.

The amines to be added to the reaction system of this invention are monodentate tertiary amines having a basicity constant (pKa) of at least 7, and the addition of such amines can result in a significant increase in the reaction rate without decrease in the selectivity. This phenomenon is quite unexpected and surprising in view of the fact known in the art that the rate of n-octadienol formation and the selectivity toward n-octadienol significantly decrease upon the addition of even a small amount of triethylamine (pKa 10.67).

The monodentate tertiary amines useful in the present invention include tri(lower)alkylamines such as trimethylamine, triethylamine, tri-n-propylamine, tri-n-butylamine, etc.; aminoalcohols such as 1-N,N-dimethylamino-2-propanol, N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, N,N,N'N'-tetramethyl- 1,3-butanediamine and the like. Among these, triethylamine is most preferred in view of various factors including reaction yield, boiling point, solubility and cost. The tertiary amine is generally added in an amount of 1 to 50% by volume based on the sulfolane.

In accordance with the process of this invention, carbonate and/or bicarbonate ions are present along with the tertiary amine to accelerate the rate of n-octadienol formation. Carbonate and bicarbonate ions are conveniently derived from carbon dioxide, sodium bicarbonate or formic acid which releases these ions in the reaction system. Among these, carbon dioxide is most preferred. In the reaction system carbonate and bicarbonate ions react with the tertiary amine to form a carbonate and/or bicarbonate of the amine.

Accordingly, the tertiary amine is reacted with carbonate and/or bicarbonate ions prior to reaction with butadiene to form the carbonate and/or bicarbonate salt of the amine, which is then added to the reaction system. In view of reaction yield, the carbonate and/or bicarbonate of the tertiary amine should be present in the reaction system in an amount of 2 to 30%, preferably 5 to 20% by weight of the reaction mixture. The proportion of the carbonate and/or bicarbonate of the tertiary amine present under the reaction conditions will depend on the temperature and the absolute partial pressure of carbon dioxide in the system. Therefore, the reaction is usually carried out under pressure so as to maintain the absolute partial pressure of carbon dioxide at about 1 to 10 kg/cm$^2$. The carbonate and/or bicarbonate ions are not consumed as n-octadienol is formed.

Any commercially available butadiene, for example, a polymerization grade or chemical reaction grade butadiene or a hydrocarbon mixture usually called "C$_4$-fraction", may be used. Preferably a polymerization grade or chemical reaction grade butadiene is used in view of reaction rate and ease in recovery of unreacted butadiene considerations. The amount of butadiene employed is not critical, but there is a limit to the solubility of butadiene in aqueous sulfolane solutions so that excess butadiene will exist in two different phases in the reaction system. For this reason, the reaction is usually carried out with butadiene being continuously or intermittently introduced into the reaction system so as to maintain the concentration of butadiene in the reaction mixture at 0.1 to 10%, preferably 1 to 5% by weight.

The aqueous sulfolane solution in the process of the present invention has a water to sulfolane weight ratio in the range of 20:80 to 70:30, preferably in the range of 25:75 to 60:40.

The n-octadienol synthesis according to the process of this invention is most preferably carried out under the conditions which meet all of the following requirements: (1) the concentration of the palladium or palladium compound is in the range of 0.5 to 20 milligrams as palladium atom per liter of the aqueous sulfolane solution; (2) the monodentate phosphine is used in an amount of 10 to 50 moles per gram atom of the palladium; (3) the carbonate and/or bicarbonate of the tertiary amine is used in an amount of 2 to 30% by weight based on the weight of the reaction mixture; (4) the amount of water present in the reaction system is 25 to 60% by weight based on the weight of the reaction mixture; and (5) the amount of sulfolane present in the reaction system is 30 to 65% by weight based on the weight of the reaction mixture.

The synthesis of n-octadienol in step (i) of the process of this invention is usually carried out by introducing butadiene into an aqueous sulfolane solution containing palladium catalyst, monodentate phosphine, tertiary amine and carbonate and/or bicarbonate ions. The reaction is carried out at a temperature of 10° to 150° C., preferably 20° to 120° C., and more preferably 50° to 110° C. Any gas-liquid contact type reactor known per se such as a stirring type reactor, an air-lift type reactor or the like may be used. The reaction may be conducted either batchwise or continuously, but a continuous process is more preferable from the viewpoint of commercial operation.

The desired product, n-octadienol, is subsequently separated by contacting at least a part of the reaction mixture obtained in step (i) to a hydrophobic membrane separator device which is capable of separating the metal-ligand complex catalyst from the n-octadienol product and unreacted butadiene feed by means of perstraction. The retentate which comprises the metal-ligand complex catalyst and varying amount of the butadiene sweep solvent is preferably recycled to the n-octadienol synthesis step. The permeate of n-octadienol product and unreacted butadiene feed is typically sweep away from the membrane by a butadiene sweep solvent.

The permeate is preferably delivered to a distillation column for separation of the n-octadienol product from the butadiene. The n-octadienol product is taken out overhead and the butadiene is taken out as bottoms which may thereafter be recycled to the n-octadienol synthesis step.

Hydrophobic membrane is preferably selected from the group consisting of: a high density polyethylene crosslinked membrane, a natural latex rubber membrane, a polyvinylidene difluoride membrane, a polychlorotrifluoroethylene membrane, a polytetrafluoroethylene membrane, a bromobutyl rubber crosslinked with hexamethylene diamine, and a copolymer of isobutylene and p-bromomethyl styrene crosslinked with hexamethylene diamine.

The n-octadienol prepared in accordance with the process of the present invention may be hydrogenated into n-octanol by any method known, although it may be used as a starting material for the preparation of chemicals as it is.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A method for separating a water soluble noble metal catalyst from a crude reaction product of a noble metal-catalyzed process for preparing octadienol from butadiene in aqueous solution, in an aqueous emulsion or as an aqueous suspension, said crude reaction product including an aqueous phase containing a water soluble Group VIII noble metal-ligand complex catalyst, and an organic phase containing unreacted butadiene feed and an octadienol reaction product, which comprises: (a) contacting said crude reaction product with a hydrophobic membrane capable of allowing a substantial portion of said unreacted butadiene feed and octadienol reaction product to pass therethrough while retaining a substantial portion of said water soluble Group VIII noble metal-ligand complex catalyst; (b) removing unreacted butadiene feed and said octadienol reaction product which passes through said hydrophobic membrane as permeate; and (c) retaining said water soluble Group VIII noble metal-ligand complex catalyst as retentate.

2. The method according to claim 1 wherein said Group VIII noble metal is either palladium or palladium compounds.

3. The method according to claim 1 wherein said ligand is a water soluble phosphine.

4. The method according to claim 3 wherein said water soluble phosphine is a sulfonated or carboxylated triaryl phosphine.

5. The method according to claim 4 wherein said water soluble phosphine is a monodentate phosphine of the formula:

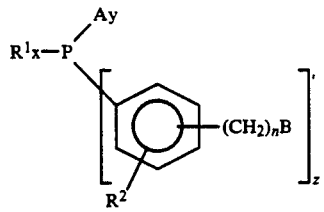

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$; wherein

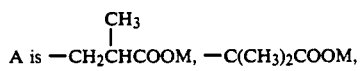

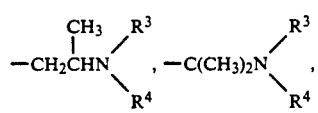

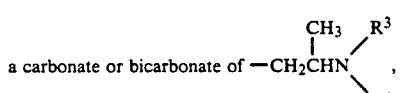

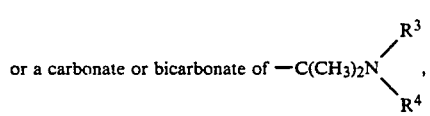

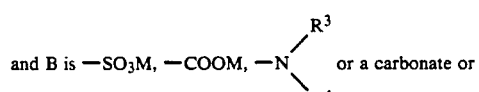

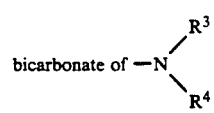

wherein R3 and R4 are each methyl, ethyl or n-propyl and M is an alkali metal in an amount of at least 6 moles per gram atom of palladium.

6. The method according to claim 1 wherein said hydrophobic membrane is selected from the group consisting of: a high density polyethylene crosslinked membrane, a natural latex rubber membrane, a polyvinylidene difluoride membrane, a polychlorotrifluoroethylene membrane, a polytetrafluoroethylene membrane, a bromobutyl rubber crosslinked with hexamethylene diamine, and a copolymer of isobutylene and p-bromomethyl styrene crosslinked with hexamethylene diamine.

7. The method according to claim 1 wherein said n-octadienol product and unreacted butadiene feed are permeated through said hydrophobic membrane by means of either perstraction or pervaporation.

8. A method for producing n-octadienol which comprises:

(i) reacting butadiene with water in an aqueous sulfolane solution having a water to sulfolane weight ratio in the range of 20:80 to 70:30 and containing carbonate and/or bicarbonate ions in the presence of (A) palladium or a palladium compound, (B) a monodentate phosphine of the formula:

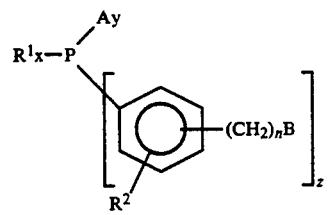

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$; wherein

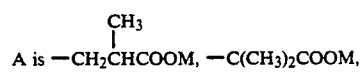

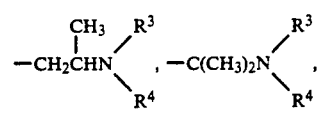

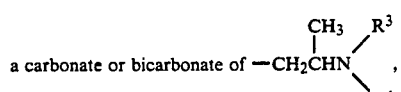

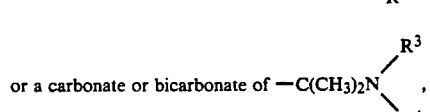

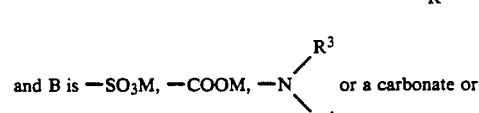

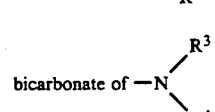

wherein R3 and R4 are each methyl, ethyl or n-propyl and M is an alkali metal in an amount of at least 6 moles per gram atom of palladium and (C) a monodentate tertiary amine having a basicity constant (pKa) of 7 or more in amount of 1 to 50% by volume based on the sulfolane to form n-octadienol;

(ii) removing the palladium-phosphine complex catalyst from said crude reaction product of step (i) by feeding said crude reaction product to a membrane separator which comprises a hydrophobic membrane capable of allowing a substantial portion of said octadienol reaction product and unreacted butadiene feed to pass therethrough while retaining a substantial portion of said palladium-phosphine complex catalyst;

(iii) recovering said octadienol reaction product and unreacted butadiene feed as permeate;

(iv) retaining said palladium-phosphine complex catalyst as retentate, wherein said hydrophobic membrane retains at least about 99% of said palladium-phosphine complex catalyst; and (v) recycling the retained palladium-phosphine complex catalyst to step (i).

9. The method according to claim 8 further comprising the step of passing the permeate of octadienol reaction product and unreacted butadiene to a distillation section wherein said octadienol is separated from said unreacted butadiene.

10. The method according to claim 9 further comprising the step of recycling said unreacted butadiene to step (i).

11. The method according to claim 8 wherein said hydrophobic membrane is selected from the group consisting of: a high density polyethylene crosslinked membrane, a natural latex rubber membrane, a polyvinylidene difluoride membrane, a polychlorotrifluoroethylene membrane, a polytetrafluoroethylene membrane, a bromobutyl rubber crosslinked with hexamethylene diamine, and a copolymer of isobutylene and p-bromomethyl styrene crosslinked with hexamethylene diamine.

12. The method according to claim 8 wherein said n-octadienol product and said butadiene feed are permeated through said hydrophobic membrane by means of either perstraction or pervaporation.

13. The method according to claim 8 wherein said tertiary amine is selected from the group consisting of: tri(lower)alkylamines, aminoalcohols, N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, and N,N,N'N'-tetramethyl-1,3-butanediamine.

14. The method according to claim 8 wherein said carbonate and/or bicarbonate ion is derived from carbon dioxide, sodium bicarbonate or formic acid.

15. The method according to claim 8 wherein said crude reaction product is separated into an aqueous layer and a organic layer before it is fed to said membrane separator.

16. The method according to claim 15 wherein said organic layer is fed to said membrane separator.

17. A method for producing n-octadienol which comprises:

(i) reacting butadiene with an aqueous solution in the presence of a water soluble Group VIII noble metal-ligand complex catalyst to form an octadienol reaction product;

(ii) separating said water soluble Group VIII noble metal-ligand complex catalyst from said octadienol reaction product of step (i) by feeding said octadienol reaction product to a membrane separator which comprises a hydrophobic membrane capable of allowing a substantial portion of said octadienol reaction product and unreacted butadiene feed to pass therethrough while retaining a substantial portion of said water soluble Group VIII noble metal-ligand complex catalyst;

(iii) recovering said octadienol reaction product and unreacted butadiene feed as permeate;

(iv) retaining said water soluble Group VIII noble metal-ligand complex catalyst as retentate, wherein said hydrophobic membrane retains at least about 99% of said water soluble Group VIII noble metal-ligand complex catalyst; and (v) recycling the retained water soluble Group VIII noble metal-ligand complex catalyst to step (i).

18. The method according to claim 17 further comprising the step of passing the permeate of octadienol reaction product and unreacted butadiene to a distillation section wherein said octadienol reaction product is separated from said unreacted butadiene.

19. The method according to claim 18 further comprising the step of recycling said unreacted butadiene to step (i).

20. The method according to claim 17 wherein said hydrophobic membrane is selected from the group consisting of: a high density polyethylene crosslinked membrane, a natural latex rubber membrane, a polyvinylidene difluoride membrane, a polychlorotrifluoroethylene membrane, a polytetrafluoroethylene membrane, a bromobutyl rubber crosslinked with hexamethylene diamine, and a copolymer of isobutylene and p-bromomethyl styrene crosslinked with hexamethylene diamine.

21. The method according to claim 17 wherein said n-octadienol product and said butadiene feed are permeated through said hydrophobic membrane by means of perstraction.

22. The method according to claim 17 wherein said aqueous solution is water in an aqueous sulfolane solution having a water to sulfolane weight ratio in the range of 20:80 to 70:30 and containing carbonate and/or bicarbonate ions.

23. The method according to claim 17 wherein said water soluble Group VIII noble metal catalyst is palladium or a palladium compound.

24. The method according to claim 17 wherein said ligand is a monodentate phosphine of the formula:

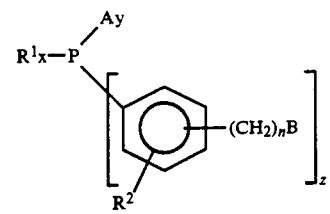

wherein $R^1$ is an aliphatic, alicyclic or substituted or unsubstituted aromatic hydrocarbon group having 1 to 8 carbon atoms; $R^2$ is hydrogen, methyl, nitro, cyano, methoxy or halogen; n is 0 or 1, x is 0, 1 or 2, and y and z are each 0, 1, 2 or 3, with the proviso that y and z are not concurrently equal to 0 and that $x+y+z=3$; wherein

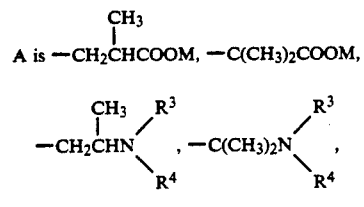

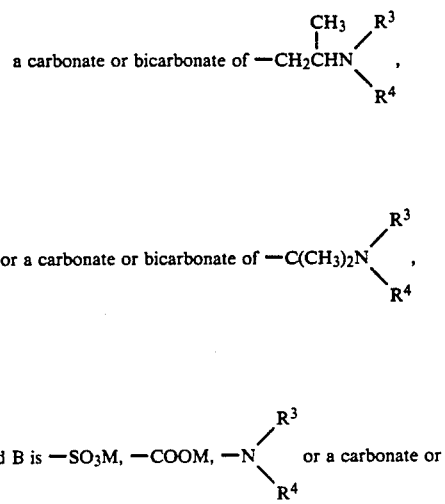

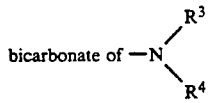

wherein $R^3$ and $R^4$ are each methyl, ethyl or n-propyl and M is an alkali metal in an amount of at least 6 moles per gram atom of palladium.

25. The method according to claim 17 further comprising addition of a monodentate tertiary amine having a basicity constant (pKa) of 7 or more in an amount of 1 to 50% by volume based on the sulfolane to form n-octadienol.

26. The method according to claim 25 wherein said tertiary amine is selected from the group consisting of: tri(lower)alkylamines, aminoalcohols, N,N-dimethyl-2-methoxyethylamine, N,N-dimethyl-3-ethoxypropylamine, N-methylpyrrolidine, N-methylpiperidine, N-methylmorpholine, N,N'-dimethylpiperazine, and N,N,N'N'-tetramethyl-1,3-butanediamine.

27. The method according to claim 22 wherein said carbonate and/or bicarbonate ion is derived from carbon dioxide, sodium bicarbonate or formic acid.

* * * * *